US007276048B2

(12) United States Patent
Enroth

(10) Patent No.: US 7,276,048 B2
(45) **Date of Patent: *Oct. 2, 2007**

(54) G-TUBE RETAINER

(76) Inventor: Lorana A. M. Enroth, 45620 Mountain View, Palm Desert, CA (US) 92260

(*) Notice: Subject to any disclaimer, the term of this patent is extended or adjusted under 35 U.S.C. 154(b) by 252 days.

This patent is subject to a terminal disclaimer.

(21) Appl. No.: 10/980,068

(22) Filed: Nov. 2, 2004

(65) Prior Publication Data

US 2005/0107745 A1 May 19, 2005

Related U.S. Application Data

(63) Continuation of application No. 09/991,233, filed on Nov. 16, 2001, now Pat. No. 6,832,993.

(51) Int. Cl.
*A61M 5/32* (2006.01)

(52) U.S. Cl. .................................................... 604/179

(58) Field of Classification Search ................ 604/174, 604/179, 270, 317, 327–329, 331–332, 341, 604/351–353, 907, 908, 910; 128/DIG. 6, 128/DIG. 26; 602/19, 36; 2/76–77, 79, 2/87, 115, 117, 308–309, 913–914, 919
See application file for complete search history.

(56) References Cited

U.S. PATENT DOCUMENTS 4,096,853 A * 6/1978 Weigand ..................... 600/431
4,248,229 A * 2/1981 Miller ........................ 604/174
4,331,144 A 5/1982 Wapner
4,959,055 A * 9/1990 Hillyer ....................... 604/179
5,496,282 A 3/1996 Militzer et al.
5,529,062 A * 6/1996 Byrd ..................... 128/207.17
5,593,389 A 1/1997 Chang
5,690,617 A 11/1997 Wright
5,884,332 A 3/1999 Snedeker
6,074,368 A 6/2000 Wright
6,077,243 A 6/2000 Quinn
6,461,319 B1 10/2002 Ekey

FOREIGN PATENT DOCUMENTS

WO WO 02/066108 * 8/2002

* cited by examiner

*Primary Examiner*—LoAn H. Thanh
(74) *Attorney, Agent, or Firm*—Orrick, Herrington & Sutcliffe LLP

(57) ABSTRACT

A gastrostomy tube retainer comprising a patient base, a venting tube extension cover connected to the patient base, and a torso wrap connected to the patient base. The patient base and venting tube extension cover protectively surround the retention button and venting tube extension of surgically implanted gastrostomy tube and are secured to the gastrostomy tube recipient by the torso wrap. In operation, the gastrostomy tube retainer tends to inhibit the non-prescribed removal of the gastrostomy tube by the tube recipient.

12 Claims, 9 Drawing Sheets

G-TUBE RETAINER

This application is a continuation application of U.S. Ser. No. 09/991,233 filed on Nov. 16, 2001 now U.S. Pat. No. 6,832,993, all of which is fully incorporated herein by reference.

FIELD OF INVENTION

The present invention relates to gastrostomy tubes and, more particularly, to a gastrostomy tube retention device that inhibits non-prescribed removal of the gastrostomy tube by the patient.

BACKGROUND OF THE INVENTION

A gastrostomy tube, commonly referred to as a "g-tube", is a tubular device that is placed in the stomach of a patient to provide the patient with essential nutrients for survival. A typical post-surgery g-tube includes a primary tube, a balloon device, a retention button, and a venting tube extension. The primary tube is placed within the stomach through a passageway cut through the abdominal and stomach walls. The balloon device inflates about the periphery of the primary tube in the stomach to anchor the primary tube in position within the stomach. The retention button is positioned about the primary tube on the exterior of the abdominal wall and, along with the balloon, sandwiches the abdominal wall to maintain the position of the primary tube in the stomach. The venting tube extension extends from the retention button outside of the body. The primary tube and venting tube extension typically include feeding, suction and inflation lumens.

It typically takes about two months for the passageway cut through the abdominal and stomach walls to form a track. During this time, and especially during the first two weeks while the wound is still fresh, it is essential that the tube not be pulled out, otherwise it could result in another surgical procedure to replace the device within hours of being pulled out. There are, however, millions of people that have g-tubes for many different reasons, most of whom are babies, toddlers, severely handicapped individuals, or elderly. Thus, a large percentage of the g-tube recipients, whether children or adults suffering from limited brain function, lack the capacity to understand not to pull on or pull out the g-tube. Unfortunately, there is no suitable means available to prevent these patients from pulling on the g-tube, whether accidentally or intentionally, which could make the area sore and/or potentially pull the g-tube out. Hospital personnel tend to respond by "rigging" available items, such as towels or blankets, together and then loosely packing these items around the g-tube. However, most patients easily remove this "rigging" in their attempts to pull the g-tube out. As a result, someone must keep watch over the g-tube patient to prevent the g-tube from being pulled out. This is especially difficult for even the most attentive caregiver.

In addition to the retention problem, there is no suitable means available to comfortably orient the g-tube in an upright and fully vented position. Hospital personnel tend to attempt a "rigging" using tape and gauze that will hold the newly placed g-tube in an upright and fully vented position. However, such a "rigging" inhibits movement of the patient more than a few inches.

Thus, it would be advantageous to provide a device that tends to prevent the patient from pulling on the g-tube and inhibit the non-prescribed removal of the g-tube.

SUMMARY OF THE INVENTION

The present invention is directed to a g-tube retainer device that tends to inhibit non-prescribed removal of a g-tube by the g-tube recipient. In a first embodiment, the g-tube retainer of the present invention includes a patient base integrally formed with an elongate venting tube extension cover. The patient base, which includes batting material, foam padding, or the like, covers a retention button of the g-tube positioned on the exterior of a patient's abdominal wall. The patient base is held in position against the patient by a torso wrap. The torso wrap is preferably adjustable with fasteners or may comprise an expandable band. The venting tube extension cover, which also includes batting material, foam padding, or the like, surrounds a substantial portion of the venting tube extension of the patient's g-tube. A passageway in the venting tube extension cover is preferably lined with a material, such as plastic and the like, that tends to slide over the g-tube venting tube extension as the g-tube recipient grabs the venting tube extension cover and attempts to pull on the g-tube venting tube extension.

In a second embodiment, the g-tube retainer of the present invention includes a patient base and an elongate venting tube extension cover. The patient base and venting tube extension cover are preferably formed as separate parts that are connectable to one another with fasteners on corresponding ends to provide for more flexibility of care by the caregiver and less disturbance of the g-tube recipient during caregiving. The fasteners may include Velcro®, snaps, buttons, hooks and loops, and the like. The patient base and extension tube cover preferably include batting material, foam padding, or the like. In an operative mode, the patient base and extension tube cover are generally tubular or cylindrical in shape and surround the g-tube retention button and venting tube extension. The patient base and extension tube cover may include fasteners, such as Velcro®, snaps, buttons, hooks and loops, that may be disengaged in a inoperative mode to enable the patient base and extension tube cover to unroll to allow for cleaning or provide other functions. Like the first embodiment, the patient base is held in position on the patient with an adjustable torso wrap and the venting tube extension cover includes a passageway that is lined with a material, such as plastic and the like, that tends to slide along the g-tube venting tube extension as the g-tube recipient grabs the venting tube extension cover and attempts to pull on the g-tube venting tube extension.

In a inoperative mode, the patient base may remain held in position and laid flat on the patient. A pouch which is attachable to the patient base while in an inoperative mode, may be utilized to neatly hold the venting tube extension in a rolled up configuration.

I another aspect, the g-tube retainer of the present invention may include a mounting loop and band to conveniently and flexibly position the g-tube and retainer in a number of desired positions for such functions as regular feeding or upright fully vented feeding.

Other aspects and features of the present invention will become apparent from consideration of the following description taken in conjunction with the accompanying drawings.

DETAILED DESCRIPTION OF THE PREFERRED EMBODIMENT

Figure 1:
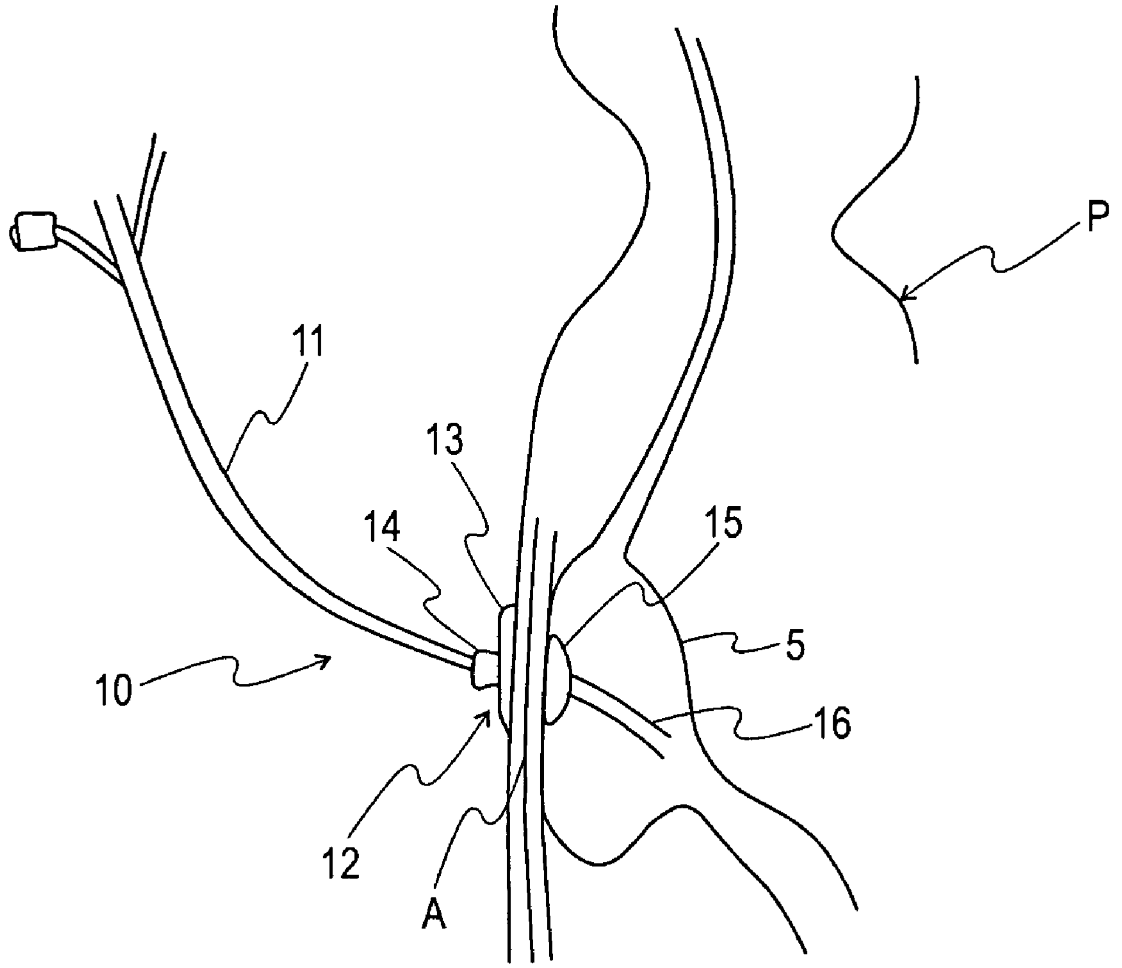
FIG. 1 is a side view of a gastrostomy tube or g-tube in the stomach of a patient.

Referring to FIG. 1, a typical gastrostomy tube or "g-tube" 10 is shown implanted in a patient P. The g-tube 10 includes a tube 16 anchored in position in the patient's stomach S with a balloon 15. The g-tube 10 is further held in position via a retention button 12 positioned exterior to the patient's abdominal wall A opposing the balloon 15. The retention button 12 comprises a base 13, typically disc-shaped, positioned against the patient's abdominal wall A and a tube neck 14 extending outwardly therefrom. A g-tube venting tube extension 11 extends from the tube neck 14.

Figure 2:
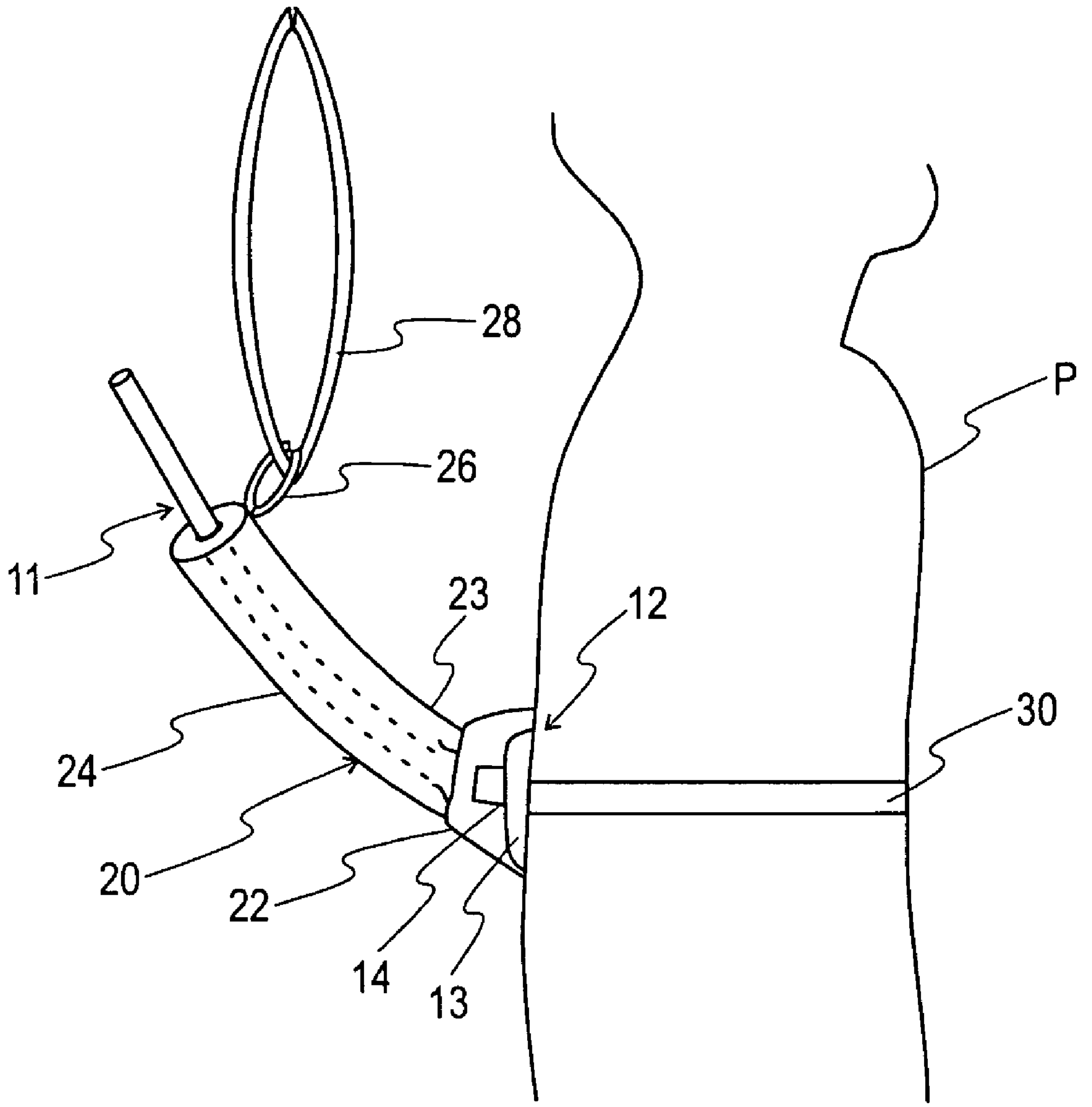
FIG. 2 is a side view of a g-tube retainer device of the present invention shown mounted over the g-tube shown in FIG. 1.
Figure 3:
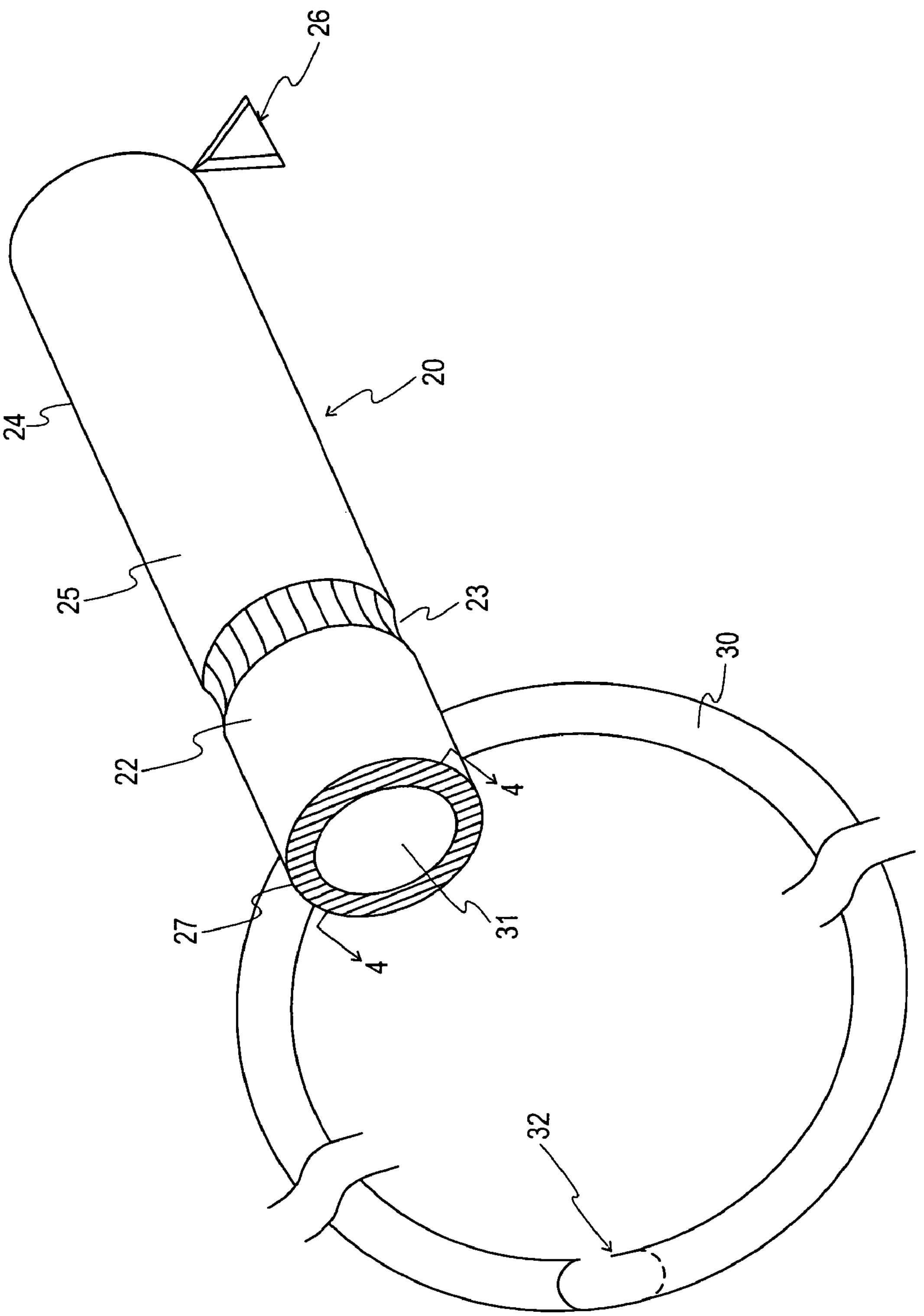
FIG. 3 is an isometric view of a first embodiment of the g-tube retainer device of the present invention.
Figure 4:
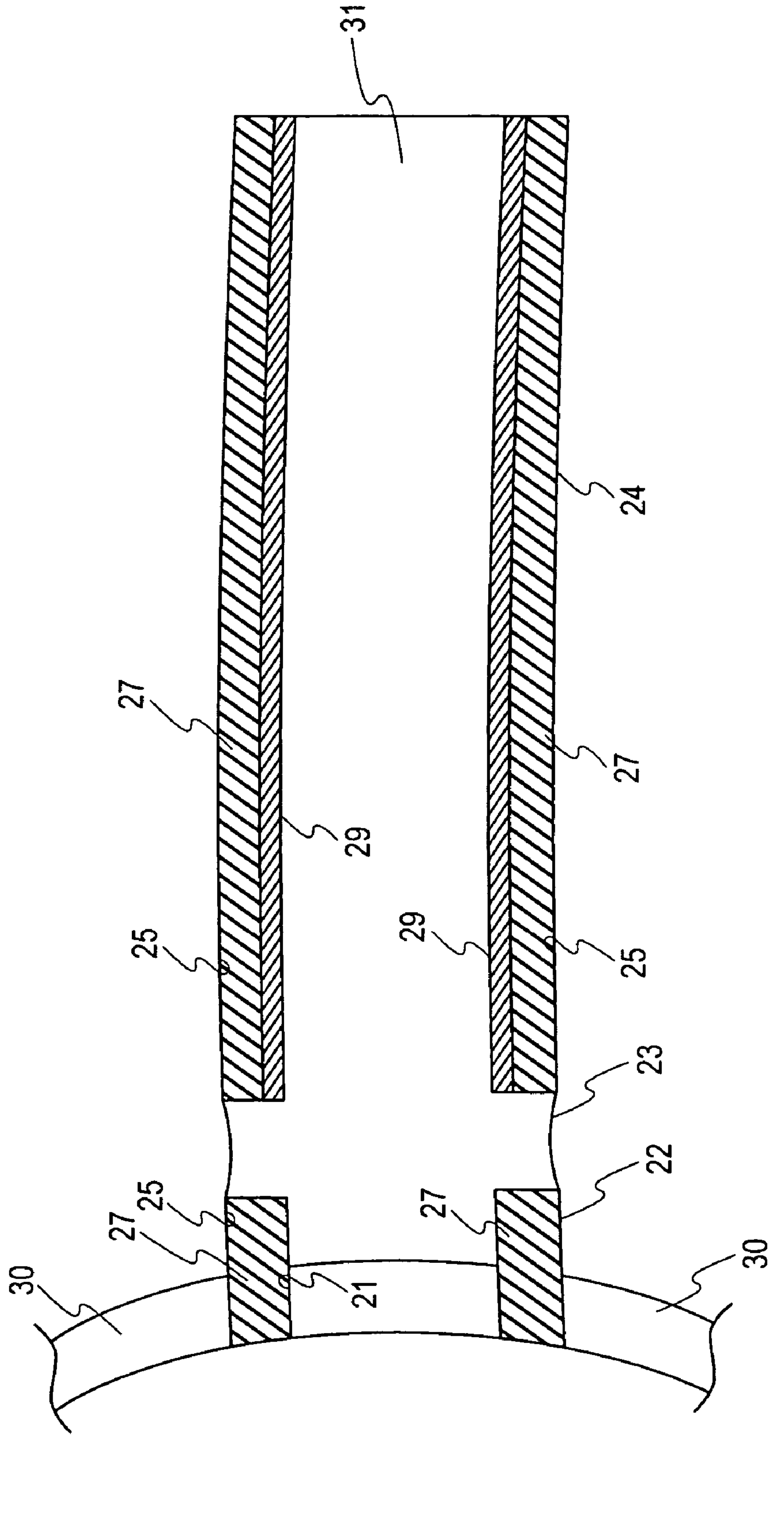
FIG. 4 is a cross-sectional view of the g-tube retainer device taken along line 4-4 in FIG. 3.

Turning to FIGS. 2-4, a first embodiment of a g-tube retention device 20 of the present invention is shown. The g-tube retainer 20 comprises a patient base 22, an elongate venting tube extension cover 24 and a transition section 23 interposing and connecting the patient base 22 and venting tube extension cover 24. The patient base 22, transition section 23 and extension cover 24 are integrally formed as a single unit. The patient base 22 is generally cylindrical in shape with an outer covering 25 preferably formed from a cotton cloth or fleece or some other non-irritating fabric or material. Batting 27 or some other padding is sandwiched between an inner covering 21 and the outer covering 25. The inner covering 21, which is formed from the same material as the outer covering 25, is fastened to the outer covering 25.

The venting tube extension cover 24 is generally cylindrical shaped elongate member with an outer covering 25 preferably formed from a cotton cloth or fleece or some other non-irritating fabric or material. As shown in the figures, the outer covering 25 for the patient base 22 and venting tube extension cover 24 is a single unit that forms the transition section 23 between the patient base 22 and extension cover 24. Like the patent base 22, batting 27 or some other padding is placed around the interior of the venting tube extension cover 24. The passageway 31 through the venting tube extension cover 24 is preferably lined with plastic sheeting or tubing 29 or other material that is slidable relative to the g-tube venting tube extension 11.

A torso wrap 30 is attached to the patient base 22 to secure the g-tube retainer 20 in place on the patient P. The torso wrap 30 may comprise an elastic band or be adjustable with a plurality of fasteners 32 attached to the ends of the wrap 30. The fasteners 32 may comprise Velcro®, snaps, buttons, hooks and loops, and the like.

In operation, the patient base 22 and venting tube extension cover 24 are slid over the g-tube venting tube extension 11 with the venting tube extension 11 passing through the plastic 29 lined passageway 31 of the venting tube extension cover 24. The patient base 22 is slid over the retention button 12 of the g-tube 10 and brought into contact with the exterior of the abdominal wall A. With the patient base 22 positioned against the exterior of the abdominal wall A and surrounding the retention button 12, the torso wrap 30 is extended around the g-tube recipient's P torso and adjusted to snugly fit around the recipient's P torso. A loop 26 attached to the proximal end of the venting tube extension cover 24 and a mounting band 28 may be used to orient the g-tube 10 and retainer 20 in a variety of desired positions to perform different functions such as regular feedings and fully vented feedings.

When installed, the g-tube retainer 20 tends to prevent the g-tube recipient from pulling on and pulling out his g-tube. Further, the padding 27 in the retainer 20 tends to inhibit the g-tube recipient from securely gripping the g-tube 10 and the g-tube venting tube extension 11. Even if the venting tube extension cover 24 is securely gripped by the g-tube recipient, the plastic sheeting or tubing 29 within the passageway 31 of the venting tube extension cover 24 tends to cause the venting tube extension cover 24 to slide relative to the venting tube extension 11, and thus prevent the g-tube 10 from being pulled out of the recipient's stomach.

Turning to FIGS. 5-10, an alternate embodiment of a g-tube retainer 120 of the present invention is shown. The g-tube retainer 120 comprises a patient base 122 and an elongate venting tube extension cover 124 that is separate from and connectable to the patient base 122. The patient base 122 includes a patient or distal end 123 and a venting or proximal end 129. The venting end 123 preferably includes a first half of a fastener or fasteners 140 such as Velcro®, snaps, buttons, hooks and loops, and the like. The venting tube extension cover 124 includes a matching or second half of a fastener or fasteners 142 mounted on the interior of a base or distal end connector flap 141. When the patient base 122 and venting tube extension cover 124 are connected by fastening fasteners 140 and 142, the g-tube retainer 120 looks similar to the g-tube retainer 20 shown in FIGS. 2 and 3.

Figure 5:
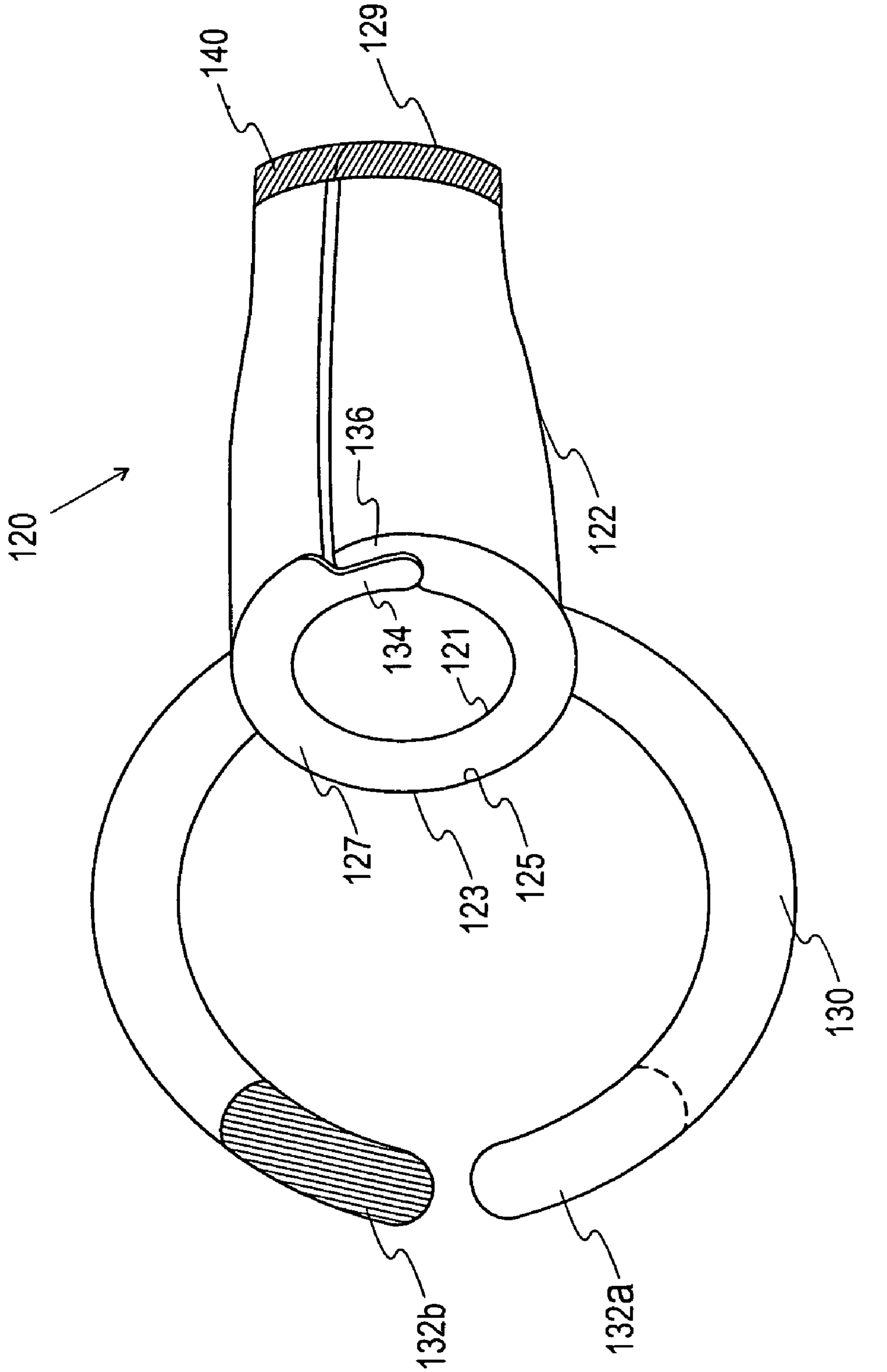
FIG. 5 is an isometric view of a patient base and torso wrap of an alternative embodiment of the g-tube retainer device of the present invention.
Figure 7B:
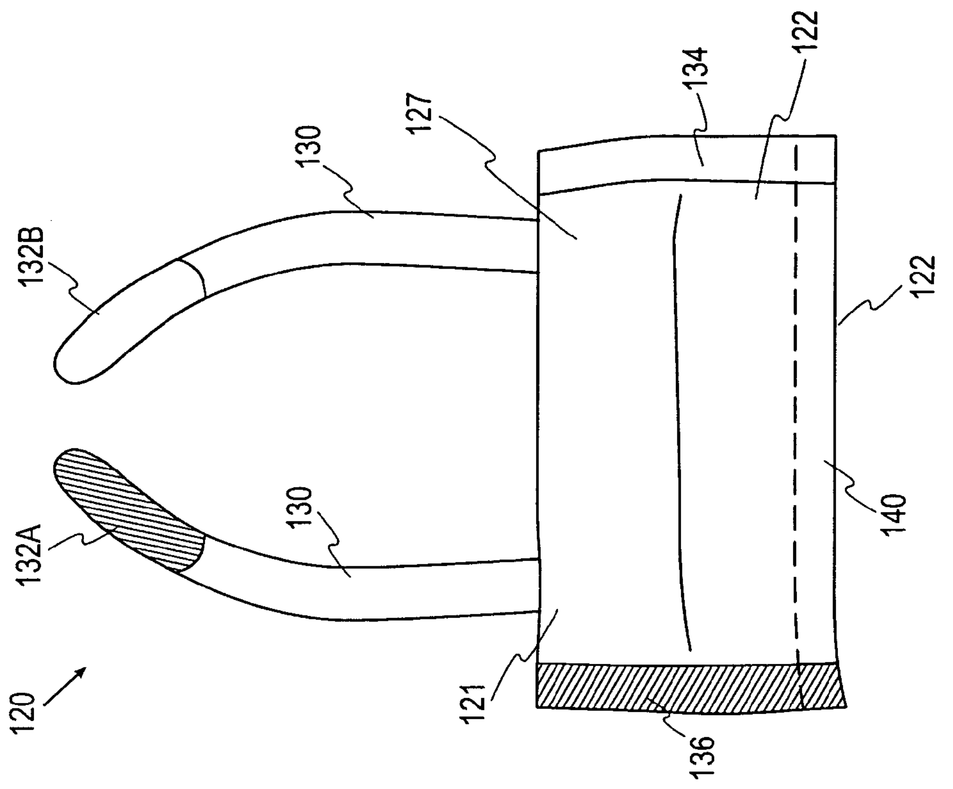
FIGS. 7*a* and 7*b* are top and bottom views, respectively, of the patient base of FIG. 5 shown in an inoperative state.
Figure 7A:
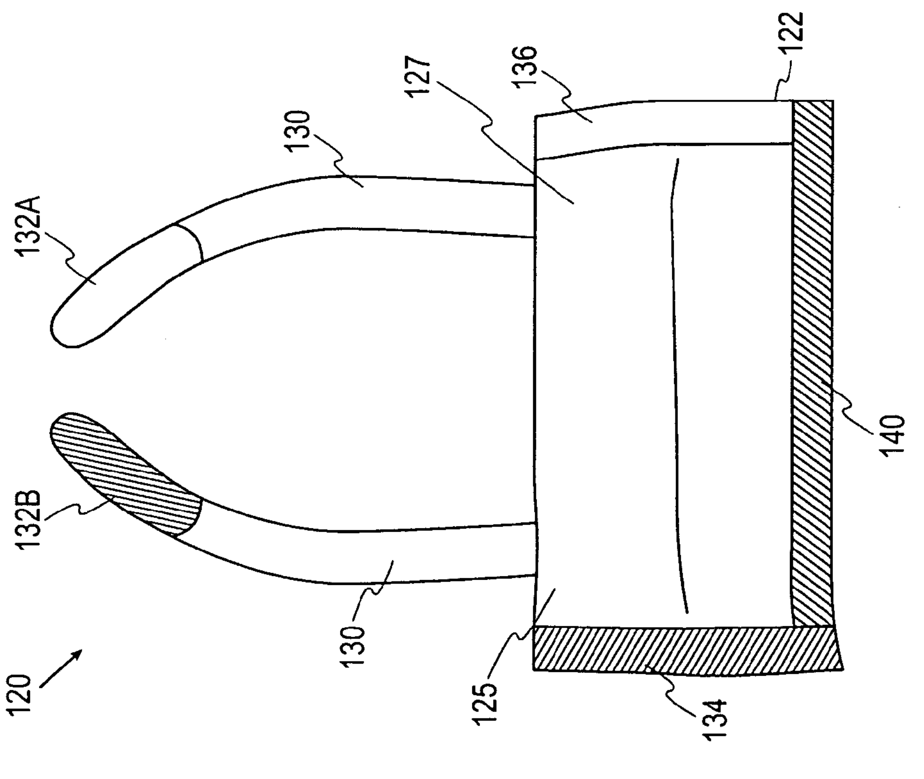

As shown in FIGS. 5, 7*a* and 7*b*, the patient base 122 may be rolled up (FIG. 5) and positioned about the retention button 12 of a g-tube 10 or unrolled (FIGS. 7*a* and 7*b*) to be cleaned or stored against the patient's body in an inoperative state. When unrolled, the patient base 122 is generally rectangular in shape. The patient base 125 includes a first or outer covering 125 and a second or inner covering 121, both preferably formed of a heavy cotton cloth or fleece or some other material or fabric that is non-irritating. The second covering 121 is attached to the first covering 125 in a manner that creates a pocket there between in which padding 127, such as batting material, foam padding, and the like, may be inserted. First and second connector flaps 134 and 136 on opposing sides of the patient base 122 include mating fasteners, such as Velcro®, snaps, button, hooks and loops, and the like, to enable the patient base 122 to be easily rolled up in a generally cylindrical shape in an operative state and unrolled in an inoperative state.

Figure 9:
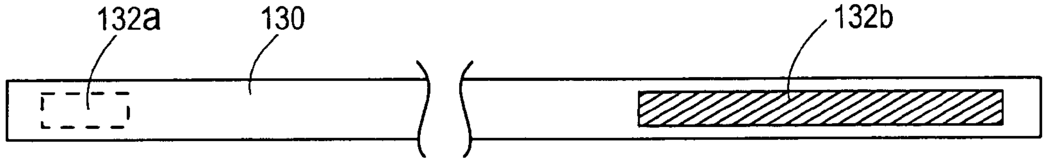
FIG. 9 is a top view of a torso wrap of the present invention.

The patient base 122 further comprises a torso wrap 130 to secure the patient base 122 in position on the patient. The torso wrap 130 connects at a first end to the patient end 123 of the patient base 122. Matching or mating fasteners 132*a* and 132*b* are attached to the torso wrap 130 at a second end. As shown in FIG. 9, the torso wrap 130 may be easily adjusted using the mating fasteners 132*a* and 132*b*.

Figure 6:
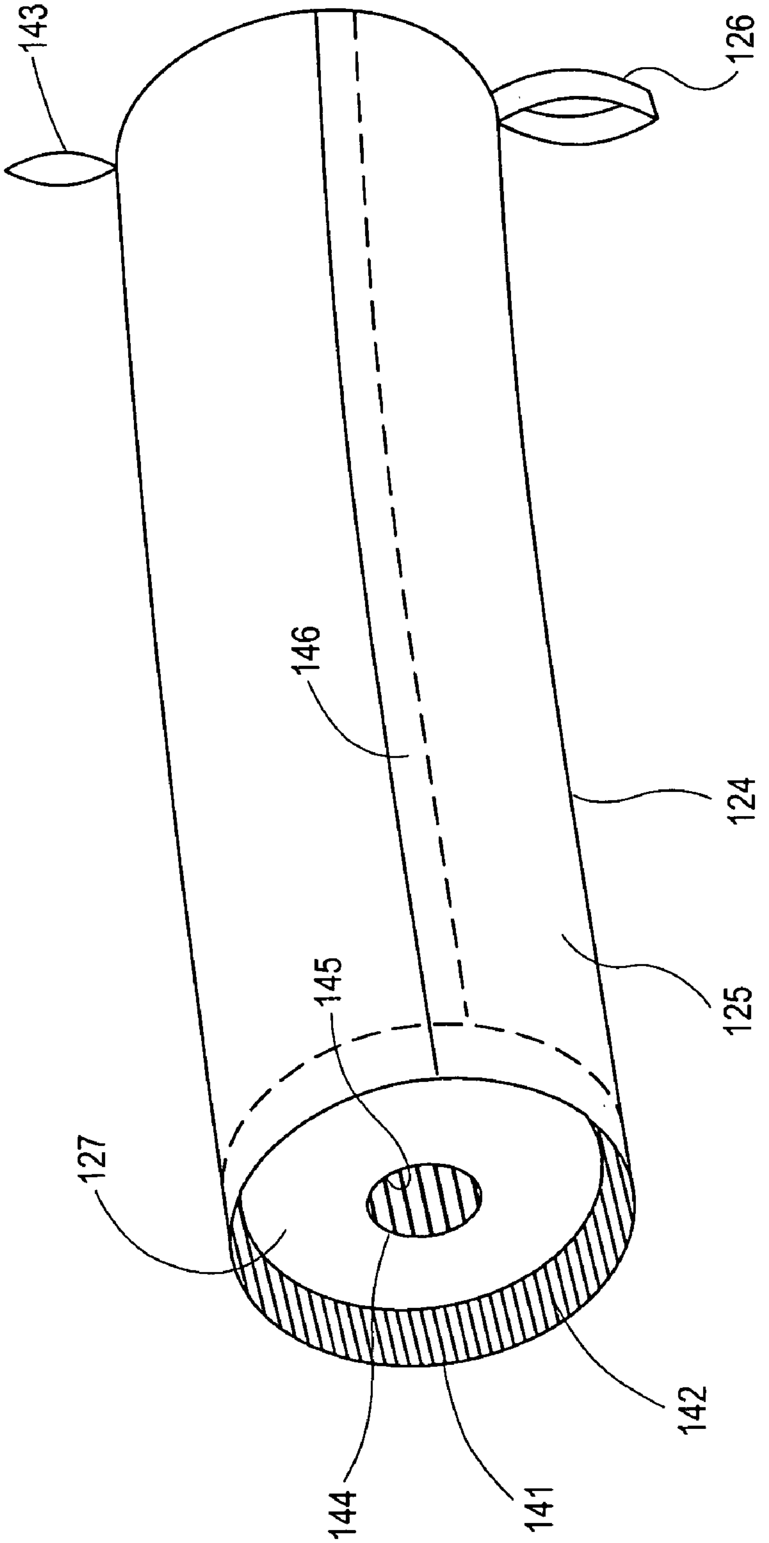
FIG. 6 is an isometric view of a venting tube extension cover of the g-tube retainer of the present invention.
Figure 8:
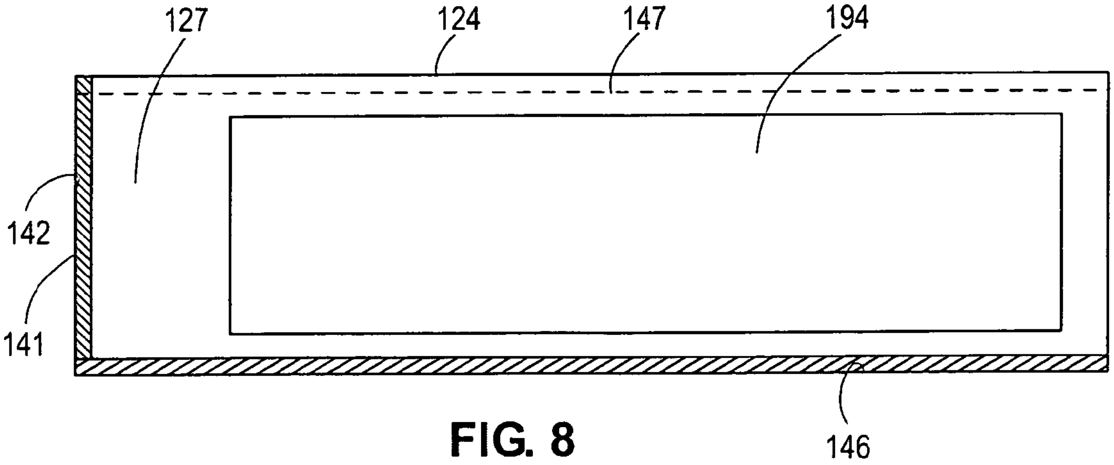
FIG. 8 is a top view of the venting tube extension cover of FIG. 6 shown in an inoperative mode.

Referring to FIGS. 6 and 8, the elongate venting tube extension cover 124 may be rolled up in an operative state (FIG. 6) or unrolled (FIG. 8) in an inoperative state to be easily cleaned or detached from the patient base 122. When unrolled, the venting tube extension cover 124 is generally rectangular in shape. The cover 124 includes an outer cover 125 preferably formed from a heavy cotton cloth or fleece or some other non-irritating material or fabric. Padding 127, such as batting material, foam, and the liked, is attached to the interior of the outer cover 125. Sheeting 144, preferably plastic or some other material that would be slidable relative to the venting tube extension 11 of the g-tube 10, is mounted over the padding 127. The venting tube extension cover 124 further comprises first and second connector flaps 146 and 147 at opposing sides of the cover 124. The flaps 146 and 147 include mating fasteners that enable the flaps 146 and 147 to be connected and hold the cover 124 in a rolled up operative state. When rolled up, the cover 124 is generally cylindrically shaped elongate member with a passageway 145, substantially lined with a sheeting material 144, extending therethrough. In an inoperative state the cover 124 may be unrolled and disconnected from the patient base 122 for cleaning.

Figure 10:
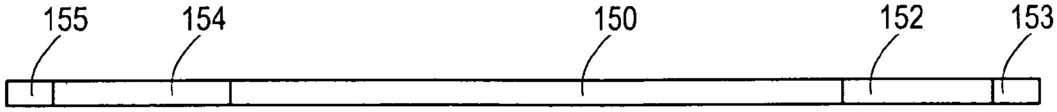
FIG. 10 is a top view of a mounting band of the present invention.
Figure 11:
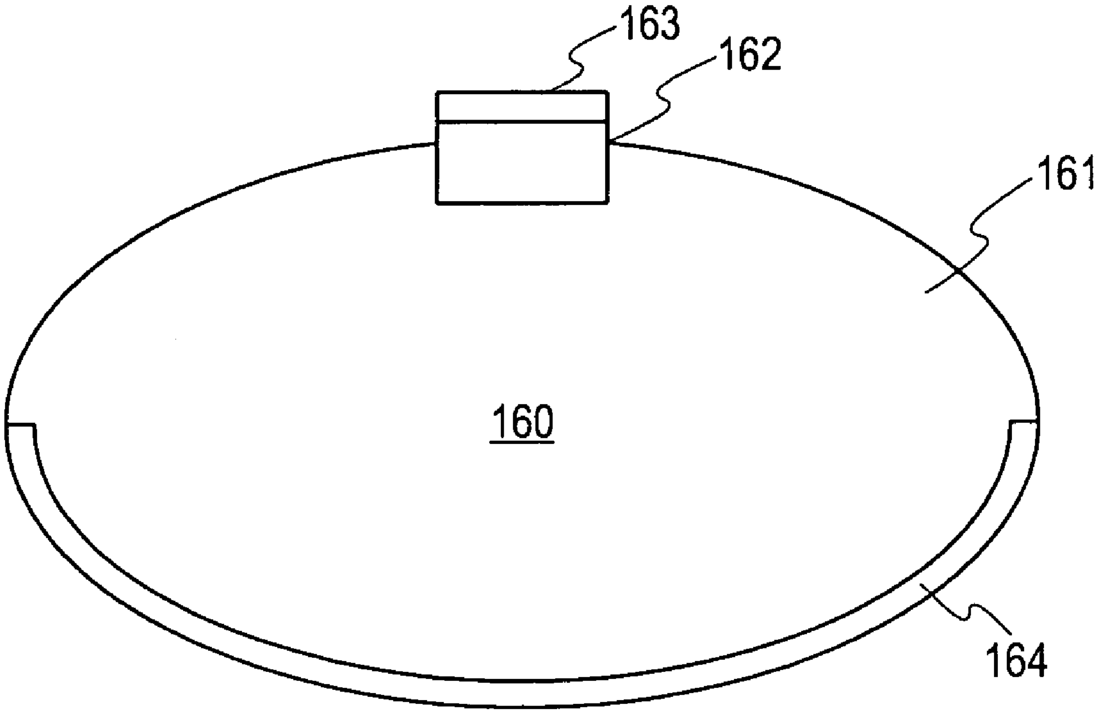
FIG. 11 is a front view of a patient base extension pouch.

The cover 124 further comprises a mounting loop 126 connected to its outermost or proximal end. The loop 126 may be used in conjunction with a mounting band 150 to secure the g-tube 10 and g-tube retainer 120 in a variety of desired positions for regular feed mode or upright fully-vented feeding mode. As shown in FIG. 10, the mounting band includes a plurality of mating fasteners such as opposing halves 152, 153, 154 and 155 of Velcro®, which enable the band 150 to be easily draped over any convenient structure and then adjusted to an appropriate length.

The cover 124 may also comprise an elastic loop 143 attached to the outermost end of the cover 124 that may be used to connect a feeding bag to the g-tube retainer 120.

In operation, the patient base 122 is positioned in an unrolled state against the patient's abdominal wall A adjacent the retention button 12 of the g-tube 10 and then rolled up to surround the button 12. The fasteners on the connector flaps 134 and 136 are fastened to secure the patient base 122 in a rolled up state. The torso wrap 130 is then extended around the patient's torso, adjusted and fastened to secure the patient base 22 in position on the patient's torso. Next, the venting tube extension cover 124 is positioned such that the connector flap 141 and fastener 142 overlap a portion of the fastener 140 on the venting end 129 of the patient base 120. Once positioned, the cover 124 is rolled up such that it surrounds the venting tube extension 11 and the connector flap 141 completely surrounds the fastener 140. The fasteners on the connector flaps 146 and 147 are fastened to secure the cover in a rolled up state and the fasteners 140 and 142 are fastened to secure the cover 124 to the patient base 122.

When installed and fully connected, the g-tube retainer 120 tends to prevent the g-tube recipient from pulling on, causing discomfort, and pulling out the g-tube. Further, the padding 127 in the cover 124 tends to inhibit the g-tube recipient from securely gripping the g-tube 10 and the g-tube venting tube extension 11. Even if the venting tube extension cover 124 is securely gripped by the g-tube recipient, the plastic sheeting 144 within the passageway 145 of the venting tube extension cover 124 tends to cause the venting tube extension cover 124 to slide relative to the venting tube extension 11, and thus prevent the g-tube 10 from being pulled out of the recipient's stomach.

In an inoperative state, the cover 124 may be removed by unfastening the fasteners on the connector flaps 146 and 147 and unfastening the fasteners 140 and 141 connecting the cover 124 to the base 122. However, the patient base 122 need not be removed from the patient, but rather it may be left in a rolled position against that patient's body for added comfort, or unrolled by unfastening the fasteners on the connector flaps 134 and 136 and then laid flat against the patient's body for future use. A base extension pouch 160 may be connected to the patient base 122 to conveniently store the venting tube extension 11 in a rolled up manner. This allows for the tube 11 to be placed in a side lying position for inoperative use of the g-tube 10 or for unvented feeding weeks later as the patient is further into recovery process. The pouch 160 comprises a base connector 162 having connector flap 163 with a fastener that is attachable to the fastener 140 on the venting end 129 of the patient base 122. The pouch 160 further includes opposing semi-circular panels 161 and detachable panel connectors 164 attached at the bottom edge of the panels 161.

While the invention is susceptible to various modifications and alternative forms, specific embodiments thereof have been shown in the drawings and are herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A gastrostomy tube retention device comprising a gastrostomy tube comprising a retention button wherein said retention button having a side for abutting an abdominal wall of a patient and an opposite side having a tube neck and an elongate venting tube extending therefrom, a cylindrical base slidable received over the retention button of the gastrostomy tube (g-tube) and configured to abut the abdominal wall of a patient, a cylindrical elongate member connected to the base and slidable received over the elongate venting tube of the g-tube and the tube neck extending from the retention button, and a torso wrap connected to the base and adjustable to secure the base in a position abutting the abdominal wall of the patient.

2. A gastrostomy tube retention device comprising a gastrostomy tube (g-tube)comprising a retention button wherein said retention button having a side for abutting an abdominal wall of a patient and an opposite side having a extension button neck and an elongate venting tube extending therefrom, a cylindrical patient base configured to abut an abdomen wall of a patient and slidably received over the retention button of the gastrostomy tube;

a transition section coupled to the patient base;

an elongate venting tube extension cover coupled to the transition section such that the transition section is interposed between the venting tube extension cover and the patient base, wherein the venting tube extension cover and transition section are configured to slidably receive a venting tube and retention button tube neck of the gastrostomy tube; and a torso wrap connected to the base and adjustable to secure the base in a position abutting the abdominal wall of the patient.

3. The retention device of claim 2, wherein the elongate venting tube extension includes an inner cover and an outer cover and padding in between the inner cover and outer cover.

4. The retention device of claim 2, wherein the torso wrap includes an elastic band.

5. The retention device of claim 2, wherein the torso wrap comprises first and second members attached at a first end to base and have matching fasteners attached to a second end of the first and second members.

6. The retention device of claim 2, further comprising a mounting loop attached to a proximal end of the elongate venting tube extension cover.

7. The retention device of claim 2, further comprising a tube extending through the elongate venting tube extension cover.

8. The retention device of claim 2, wherein the patient base and elongate venting tube extension cover are detachably connected.

9. The retention device of claim 2, wherein the patient base includes a first fastener on a proximal end and the elongate venting tube extension cover includes a second fastener on a distal end, the second is capable of mating with the first fastener.

10. The retention device of claim 9, wherein the elongate venting tube extension cover has an operative state and an inoperative state.

11. The retention device of claim 10, wherein the elongate venting tube extension cover is rolled up in a generally cylindrical shape in the operative state.

12. The retention device of claim 10, wherein the elongate venting tube extension cover is unrolled in a generally rectangular shape in the inoperative state.

* * * * *